United States Patent [19]

Napier

[11] 4,307,041
[45] Dec. 22, 1981

[54] STABILIZATION OF PHOSPHOROCHLORIDATES OR THIONOPHOSPHOROCHLORIDATES WITH PHOSPHORUS PENTACHLORIDE

[75] Inventor: Roger P. Napier, Califon, N.J.

[73] Assignee: Mobil Oil Corporation, New York, N.Y.

[21] Appl. No.: 153,302

[22] Filed: May 27, 1980

[51] Int. Cl.³ .............................. C07F 9/14; C07F 9/20
[52] U.S. Cl. .................................... 260/989; 260/960
[58] Field of Search ................................. 260/960, 989

Primary Examiner—Anton H. Sutto
Attorney, Agent, or Firm—Charles A. Huggett; Michael G. Gilman; Edward J. Trojnar

[57] ABSTRACT

Phosphorochloridates and thionophosphorochloridates are stabilized against decomposition by the addition of minor amounts of phosphorus pentachloride or the equivalent minor amount of phosphorus trichloride and chlorine. Hydrogen chloride which may be formed is removed by sparging with inert gas. The invention permits the elimination of the customary expensive distillation step previously relied on for production of a stable product to attain commercially acceptable stability to alkyl phosphorochloridates such as diethylphosphorochloridate.

8 Claims, No Drawings

STABILIZATION OF PHOSPHOROCHLORIDATES OR THIONOPHOSPHOROCHLORIDATES WITH PHOSPHORUS PENTACHLORIDE

BRIEF DESCRIPTION OF THE INVENTION

The present invention is directed to a method for stabilizing phosphorochloridates and thionophosphorochloridates during storage. Decomposition is inhibited by the addition of small amounts of phosphorus pentachloride or the equivalent thereof of phosphorus trichloride and chlorine. The addition of the stabilizers of this invention permits the elimination of the expensive distillation step used in the art to obtain stable products.

DETAILED DESCRIPTION OF THE INVENTION

It is known in the art (Bliznyaks et al, *Synthesis of Dialkyl Phosphorochloridates,* All-Union Phytopathology Research Institute, Translated from Zhurnal Obshchei Khimii, Vol. 37, 6, pp. 1353–1354, June 1967), that the yield of dialkyl phosphorochloridates resulting from chlorination of dialkyl hydrogen phosphites can be increased by the addition of compounds such as phosgene, thionyl chloride or phosphorous pentachloride to the reaction mixture prior to distillation. It is theorized that these compounds increase the yield of the phosphorochloridates and thionophosphorochloridates by reacting with intermediate complexes such as acids which are formed by the side reaction of hydrochloric acid with the product. According to the prior art, phosgene, thionyl chloride or phosphorous pentachloride react with these undesirable intermediates to form acid chlorides which are then removed by distillation so that the intermediates do not reduce the yield of product by reacting with it during storage.

Irrespective of the mode of the synthesis or resulting yield, phosphorochloridates and thionophosphorochloridates, which are intermediates in the production of certain insecticides, possess inherent instability on storage and are particularly affected by the presence of moisture as well as certain impurities.

It has been theorized that this instability of diethyl phosphorochloridate, for example, results from the following reactions:

$$(CH_3CH_2O)_2P(O)Cl + H_2O \longrightarrow (CH_3CH_2O)_2P(O)OH + HCl$$

The acid product in turn can react with additional chloridate to form

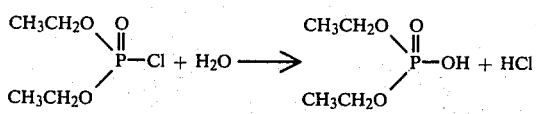

$+ HCl$

HCl produced from either of these reactions can react further with the chloridate to give

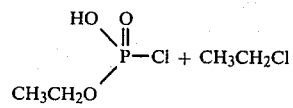

which also can then react with more chloridate to give the product:

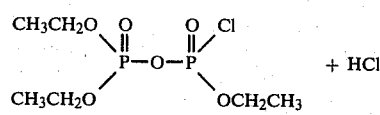

$+ HCl$

As can be seen, the dialkyl phosphorochloridate can be rapidly depleted to form unwanted by-products. This chain reaction can be initiated by water as shown above, by traces of HCl, by impurities formed in the reaction or thermally, especially at temperatures of about 25°–40° C.

Since typical production schedules require that products like diethylphosphorochloridate be stored and shipped for later use, it is of utmost importance to impart as much stability as is economically possible.

It is accordingly an object of this invention to provide a method of stabilizing phosphorochloridates and especially dialkyl phosphorochloridates, particularly against decomposition during storage.

The present invention is applicable to a wide variety of phosphorochloridates and thionophosphorochloridates which exhibit instability of the kind associated with diethyl phosphorochloridate. In general, the stabilization method of this invention can be utilized with compounds having the formula:

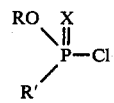

where
R is alkyl of 1–10, preferably 1–4 carbons;
R' is RO; R; aryl, particularly phenyl; aryl substituted by halogen, —NO₂, alkyl or alkoxy of 1–4 carbons; phenoxy; phenoxy substituted by halogen, —NO₂, alkyl or alkoxy of 1–4 carbons; halogen; or hydrogen; and
X is oxygen or sulfur.

The present invention is particularly concerned with stabilizing dialkyl phosphorochloridates wherein the alkyl group has 1–4 atoms, e.g., diethyl phosphorochloridate.

Stabilization according to the present invention is carried out by adding a minor amount of phosphorus pentachloride to the phosphorochloridate or thionophosphorochloridate, as prepared, without distillation to remove impurities which cause decomposition. Alternatively, phosphorus trichloride can be added followed by chlorination to produce PCl₅ in situ. The amount of PCl₅ (or equivalent PCl₃) added to effect stabilization according to the invention is about 0.07 to 1.5 weight percent based on the phosphorochloridate, preferably 0.1 to 1.0 weight percent.

Without being bound to theory or mechanistic explanation for stabilization according to the invention, it is believed that the following reactions may occur, thereby accounting for removal of reactive impurities and intermediates so that the phosphorochloridate is not destabilized.

$$H_2O + PCl_5 \rightarrow POCl_3 + 2HCl$$

dialkylphosphoric acid + $PCl_5 \rightarrow$ dialkylphosphorochloridate + HCl + $POCl_3$. monoalkyl chlorophosphoric acid + $PCl_5 \rightarrow$ monoalkylphosphorodichloridate + HCl + $POCl_3$.

Hydrochloric acid formed during these reactions can advantageously be removed by sparging with an inert gas, such as nitrogen. When treatment is carried out according to the invention, typical stabilizations have resulted with loss of phosphorochloridate of 0.05 to 0.1% per day at 40° C., which is comparable to that obtained with freshly distilled phosphorochloridate. The method of this invention constitutes a commercially important finding because the expensive distillation step can be omitted and commercially acceptable stability attained.

EXAMPLE 0.1 g of $PCl_3$ was dissolved in 15 g of raw diethylphosphorochloridate (DEPC). Chlorine gas was added until excess chlorine persisted in the DEPC. In situ formation of $PCl_5$ took place. The organic solution was sparged with an inert gas to remove traces of chlorine and as much HCl as possible. The following table described the relative stabilities of distilled DEPC, untreated DEPC, and DEPC treated according to this invention.

| 40 DAY STABILITY TESTS AT 40° C. | |
|---|---|
| SOURCE | % LOSS PER DAY |
| Distilled DEPC | 0.04 |
| Untreated DEPC | 0.40 |
| $PCl_5$ Stabilized DEPC | 0.06 |

What is claimed is:

1. A method of stabilizing phosphorochloridate or thionophosphorochloridate compounds which comprises adding to said compounds, as prepared, 0.07 to 1.5 weight percent phosphorus pentachloride without distillation to remove impurities which promote decomposition.

2. The method of claim 1 wherein said phosphorochloridate or thionophosphorochloridate compound is a dialkyl phosphorochloridate or thionophosphorochloridate with each alkyl being of 1 to 10 carbons.

3. The method of claim 1 wherein said phosphorochloridate or thionophosphorochloridate has the formula:

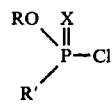

where
R is alkyl of 1–10 carbon atoms;
R' is RO—; R; aryl; aryl substituted by halogen, $-NO_2$, alkyl or alkoxy of 1–4 carbons; phenoxy; phenoxy substituted by halogen, $-NO_2$, alkyl or alkoxy of 1–4 carbons; halogen; or hydrogen; and
X is oxygen or sulfur.

4. The method of claim 3 wherein R is alkyl of 1–4 carbons;
R' is RO—; and
X is oxygen.

5. The method of claim 3 wherein said phosphorochloridate is diethyl phosphorochloridate.

6. The method of claim 1 in which phosphorus pentachloride is added to said phosphorochloridate or thionophosphorochloridate.

7. A method of stabilizing phosphorochloridate or thionophosphorochloridate compounds which comprises adding to said compounds, as prepared, 0.07 to 1.5 weight percent of phosphorus pentachloride, in the form of phosphorus trichloride and chlorine, and sparging with inert gas to remove HCl formed without distillation to remove impurities which promote decomposition.

8. The method of claim 3 wherein R is alkyl of 1–4 carbons;
R' is RO—; and
X is oxygen.

* * * * *

UNITED STATES PATENT AND TRADEMARK OFFICE
CERTIFICATE OF CORRECTION

PATENT NO. : 4,307,041
DATED : December 22, 1981
INVENTOR(S) : Roger P. Napier

It is certified that error appears in the above-identified patent and that said Letters Patent are hereby corrected as shown below:

Claim 2 should be dependent on both claims 1 and 7.

Claim 3 should be dependent on both claims 1 and 7.

Claim 8 should be cancelled as duplicate of Claim 4,

On The Title Page, "8 Claims, No Drawings" should read -- 7 Claims, No Drawings --.

Signed and Sealed this

Eleventh Day of May 1982

[SEAL]

Attest:

GERALD J. MOSSINGHOFF

*Attesting Officer*     *Commissioner of Patents and Trademarks*